United States Patent [19]
Pace

[11] Patent Number: 5,484,414
[45] Date of Patent: Jan. 16, 1996

[54] SYRINGE INCORPORATING A SELF-CONTAINED RETRACTABLE NEEDLE

[76] Inventor: Paul A. Pace, 610 67th St., Brooklyn, N.Y. 11220

[21] Appl. No.: 309,726

[22] Filed: Sep. 21, 1994

[51] Int. Cl.⁶ ........................................ A61M 5/00
[52] U.S. Cl. ........................... 604/110; 604/195
[58] Field of Search ............................. 604/195, 187, 604/110, 218, 228, 198, 263

[56] References Cited

U.S. PATENT DOCUMENTS

| | | | |
|---|---|---|---|
| 4,677,980 | 7/1987 | Reilly et al. | 604/228 X |
| 4,911,695 | 3/1990 | Lindner | 604/228 |
| 4,919,657 | 4/1990 | Haber et al. | 604/232 |
| 4,950,251 | 8/1990 | Haining | 604/195 |
| 5,098,402 | 3/1992 | Davis | 604/195 |
| 5,190,526 | 3/1993 | Murray et al. | 604/110 |
| 5,242,419 | 9/1993 | Kiner et al. | 604/218 X |
| 5,346,474 | 9/1994 | King | 604/110 |

*Primary Examiner*—John D. Yasko
*Attorney, Agent, or Firm*—Richard L. Miller

[57] ABSTRACT

The invention is a syringe with a retractable needle, comprising a syringe housing having a bore, a needle assembly within the bore, and a plunger assembly extending into the bore. The plunger assembly has a rectangular key. The needle assembly has a key hole which matches the key, so that the key may be inserted into the key hole. After conventional use the plunger is rotated to lock the key within the key hole, and the plunger withdrawn to retract the needle through a resilient elastomeric seal into the syringe, rendering it inoperable and harmless.

1 Claim, 1 Drawing Sheet

U.S. Patent  Jan. 16, 1996  5,484,414
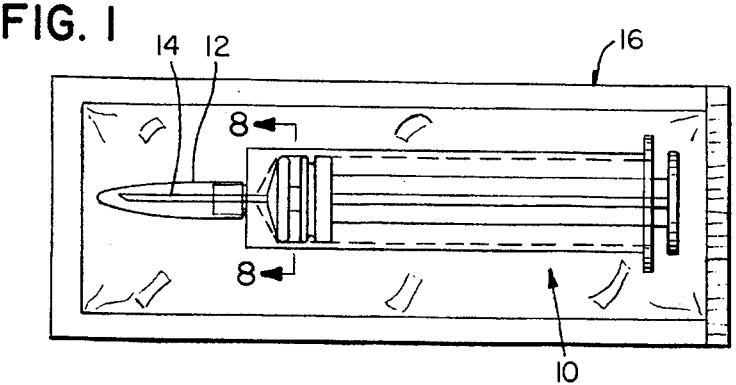
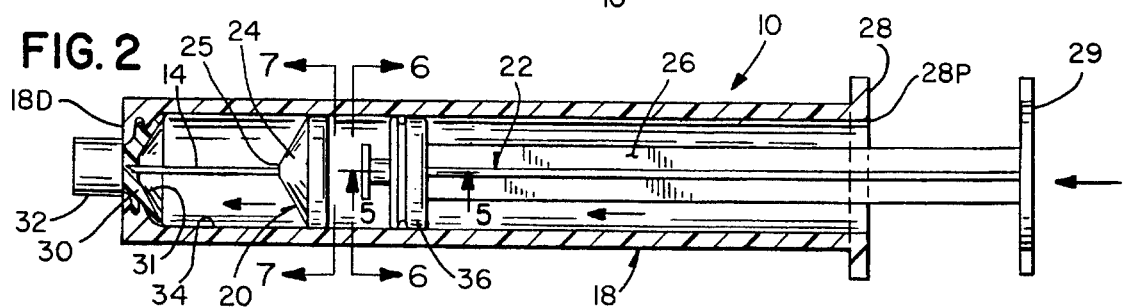

SYRINGE INCORPORATING A SELF-CONTAINED RETRACTABLE NEEDLE

BACKGROUND OF THE INVENTION

The invention relates to a self-contained syringe with retractable needle. More particularly, the invention relates to a medical and industrial device used for administering or receiving fluids to or from a patient, area or process and more specifically a syringe with a mechanical system for automatically retracting the needle into the syringe, thereby rendering the syringe harmless and inoperable.

Due to the recent and rapid spread of such communicable diseases as AIDS and Hepatitis, the need for a safe, self-contained syringe with a retracting needle is apparent. Health care workers such as doctors, nurses, lab analysts and the like are constantly faced with the threat of contracting such diseases via contaminated blood which may be present on the end of a needle which might accidentally puncture their skin. Sanitation and medical waste disposal personnel are also faced with the same danger.

In addition, the costs of disposing of such conventional syringes is becoming prohibitive, due to the fact that they must be transported in thick plastic receptacles, handled with extreme care, and disposed of in only designated waste facilities.

Furthermore, conventional syringes are a large contributor to the spread of diseases such as AIDS and Hepatitis among intravenous drug users. By re-using syringes with contaminated needles, these drug users have greatly increased the spread of blood transported infectious diseases.

The incidence of injury to life and health by the spread of infected blood present on such syringe needles is greater today than ever before. The need for a safe, reliable, inexpensive and manufacturable syringe with retracting needle is of significant importance.

U.S. Pat. No. 5,190,526 to Murray et al., discloses a hypodermic syringe having a complicated needle retracting system requiring many working parts.

U.S. Pat. No. 4,950,251 to Haining, discloses a retractable needle syringe.

U.S. Pat. No. 4,919,657 to Haber et al., discloses a reusable dental syringe having a retractable needle.

While these units may be suitable for the particular purpose employed, or for general use, they would not be as suitable for the purposes of the present invention as disclosed hereafter.

SUMMARY OF THE INVENTION

It is an object of the present invention to produce a self-contained syringe with a retractable needle.

It is another object of the invention to produce a self-contained syringe with a retractable needle which, by allowing the needle to retract fully into the syringe after use, renders the needle incabable of accidentally puncturing the skin of a health care worker, lab worker, etc. Accordingly, the risk of spreading communicable diseases via contaminated blood on the tip of the needle is significantly decreased, if not nullified.

It is a further object of the invention to produce a self-contained syringe with retractable a needle which, in addition to decreasing the risk of infection to health care and medical professionals, also offers the benefit of ease of disposal. Unlike present syringes which must be disposed of in hard-plastic waste containers which are designed to avoid puncture by the needle, this apparatus can be disposed of in a light-weight hazardous waste bag, with no fear of the needle penetrating or puncturing the bag. Furthermore, this apparatus can be directly disposed in conventional waste baskets, if so desired.

It is a still further object of the invention to produce a self-contained syringe with retractable needle which, by allowing the needle to retract fully into the syringe after use, renders the syringe inoperable, so that it may not be inadvertently or intentionally re-used. Thus, the possibility that a medical worker might inadvertently use an infected syringe more than once is eliminated. Also eliminated is the opportunity for intravenous drug users to share or re-use infected needles.

The invention is a syringe with a retractable needle, comprising a syringe housing having a bore, a needle assembly within the bore, and a plunger assembly extending into the bore. The plunger assembly has a rectangular key. The needle assembly has a key hole which matches the key, so that the key may be inserted into the key hole, the plunger rotated to lock the key within the key hole, and the plunger withdrawn to retract the needle assembly into the syringe, rendering it inoperable and harmless.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a diagrammatic plan view of the instant invention sealed in a sterilized package;

FIG. 2 is a diagrammatic plan view of the instant invention with parts in section;

FIG. 3 is a diagrammatic perspective view with parts broken away to better illustrate the internal construction therein;

FIG. 4 is an enlarged cross-sectional view with parts broken away taken on line 4—4 of FIG. 3 with the needle and plunger locked together and the needle fully extended;

FIG. 5 is a still further enlarged cross sectional view with parts broken away taken on line 5—5 of FIG. 2;

FIG. 6 is a cross sectional view with parts broken away taken on line 6—6 of FIG. 2;

FIG. 7 is a cross sectional view taken on line 7—7 of FIG. 2;

FIG. 8 is a cross sectional view with parts broken away taken on line 8—8 of FIGS. 1 and 6; and FIG. 9 is an enlarged cross sectional view taken on line 9—9 of FIG. 7 with parts broken away.

DETAILED DESCRIPTION OF THE PREFERRED EMBODIMENTS

FIG. 1 illustrates a syringe 10 having a needle 14 with a protective sheath 12 surrounding the needle 14. Prior to use, the syringe 10 is sealed in a sterilized package 16.

Referring to FIG. 2, the syringe 10 comprises a syringe housing 18, a needle assembly 20, and a plunger assembly 22.

The syringe housing 18 has a proximal end 28P and a distal end 18D. The syringe housing 18 comprises a finger flange 28 at the proximal end 28P of the syringe housing 18 and a resilient elastomeric seal 30 embedded inside the distal end 18D of the syringe housing 18. The resilient elastomeric seal 30 tapers inward and mates with a circular nose 32 located at the distal end 18D, through which the needle 14 extends. Annular flange 42 formed integrally with resilient elastomeric seal 30 interlocks with annular flange 44 formed integrally with the syringe housing 18. The syringe housing 18 has a bore 34 through the center, which is machined smooth. The bore 34 extends into the syringe housing 18 from the proximal end 28P of the syringe housing 18 where the finger flange 28 is located. The bore 34 tapers down to a diameter just larger than the diameter of the needle 14 at the distal end 18D of the syringe housing 18 where the circular nose 32 is located.

The needle assembly 20 has a needle seat 24, which is conical shaped, having an apex 25. The needle 14 extends into the needle seat 24, through the apex 25.

The syringe housing has a forward cone 31 in the bore 34 at the distal end 18D which mates with the conical shape of the needle seat 24, to ensure stability and rigidity of the needle 14 during injections.

The plunger assembly 22 comprises a stem 26 which runs through the bore 34 of the syringe housing 18, and protrudes outside of the syringe housing 18 at the proximal end 28P. A thumb plate 29 is secured to an end of the stem 26 that protrudes outside of the syringe housing 18 at the proximal end 28P. A piston 36 is secured to an opposite end of the stem 26, such piston 36 having a diameter that is slightly less than that of the bore 34 to allow slidable movement within the bore 34 while preventing fluid leakage between the piston 36 and the bore 34. The piston 36 has a smooth finish to facilitate the sliding of the piston 36 into the bore 34 when pressure is applied to the thumb plate 29.

FIG. 3 is a perspective view of the syringe 10, and illustrates the mating of the piston 36 with the needle seat 24. By mating the piston 36 and the needle seat 24, the needle 14 may be fully retracted within the syringe housing 18 by pulling on the thumb plate 29, thus rendering the syringe 10 inoperable.

FIG. 4 is a cross sectional view with parts broken away, depicting the mating of the piston 36 with the needle seat 24 of the needle assembly 20.

FIG. 5 is a cross sectional view with parts broken away of the piston 36 within the bore 34 of the syringe housing 18. A cylindrical key shaft 37 protrudes from the piston 36 opposite the stem 26. A key 38 protrudes from the key shaft 37 opposite the piston 36.

FIG. 6 illustrates the piston 36 fitted tightly within the bore 34 of the syringe housing 18. The key 38, rectangular in shape, is shown protruding from the piston 36.

FIG. 7 is a cross sectional view of the bore 34, illustrating the needle assembly 20. A key hole 40 is located within the center of the needle seat 24. The key hole 40 is rectangular to match the key 38, and is slightly larger than the key 38.

FIG. 9 details the needle assembly 20. The needle seat 24 has a key cavity 41, which is in fluid communication with the needle 14. The key hole 40 extends into the key cavity 41. The needle 14 is shown extending through the apex 25 of the needle seat 24.

FIG. 8 is a cross sectional view with parts broken away of the needle assembly 20 within the bore 34 of the syringe housing 18. The key 38 is aligned with the key hole 40 by rotating the thumb plate 29, and is inserted through the key hole 40 into a key cavity 41 after completion of the downstroke of the plunger assembly 22 through the bore 34 of the syringe housing 18. Upon insertion of the key 38 into the key cavity 41, the thumb plate 29 is rotated, rotating the key 38 within the key hole 40, so that the key 38 is no longer aligned with the key hole 40, thus locking the needle assembly 20 and plunger assembly 22 together. By then pulling on the thumb plate 29, the needle 14 may be retracted into the syringe housing 18.

The operation of the syringe is now briefly described. The syringe is removed from its protective sterilized package 16 and protective sheath 12 surrounding the needle 14 is separated therefrom. The needle is than inserted into an appropriate source of injectable fluid. The plunger assembly 22 is withdrawn from the bore 34 to create a low pressure region within the bore 34, thus drawing fluid into the bore 34 through the needle 14. The needle 14 is inserted into the desired destination vessel, patient, etcetera and the fluid is injected by pressing the plunger assembly 22 to empty the contents of the bore 34 through the needle 14.

Once the syringe has been used, it is now desirable to make it inoperable. The plunger assembly 22 is rotated to align the key 38 with the key hole 40. The plunger assembly 22 is depressed slightly to insert the key 38 through the key hole 40 and into the key cavity 41. The plunger assembly 22 is then rotated to cause the key 38 and key hole 40 to be out of alignment, trapping the key 38 in the key cavity 41, mating the needle assembly 20 with the plunger assembly 22. Finally, the plunger assembly 22 is withdrawn to retract the needle assembly 20, out of the resilient elastomeric seal, rendering the syringe inoperable and harmless.

What is claimed is:

1. A syringe incorporating a self-contained retractable needle, comprising:

a) a syringe housing, having a proximal end and a distal end, having a bore extending into the syringe housing from the proximal end, and having a circular nose at the distal end;

b) a needle assembly, having a needle seat which is conical in shape, having an apex, and being substantially the same diameter as the piston, the needle assembly having a keyhole opposite the apex, the needle assembly further having a needle which protrudes from the apex and is in fluid communication with the keyhole, the needle extends through the circular nose when in an operable position, wherein the housing has a forward cone in the bore at the distal end which mates with the conical shape of the needle seat, to ensure stability and rigidity of the needle during injections; and c) a plunger assembly, extending into the bore, having a piston on one end and a thumb plate on an opposite end, the piston having a slightly smaller diameter than the bore for a tight fit therebetween while still allowing slidable movement of the piston within the bore, the piston having a face and having a key protruding from the face, the key being of the same shape as the key hole and being slightly smaller in size so that it when aligned the key may enter the key hole, when the key is rotated and is no longer aligned with the key hole it may not exit the key hole, thus mating the needle assembly with the plunger assembly so that the needle may be retracted into the syringe housing, wherein the key is rectangular in shape, and the key hole is rectangular in shape, wherein the key further comprises a cylindrical key shaft between the key and the piston, wherein the syringe housing has a resilient elastomeric seal embedded in said distal end of said syringe housing so that the needle may be retracted into the syringe housing.

* * * * *